(12) United States Patent
Saito et al.

(10) Patent No.: US 9,814,373 B2
(45) Date of Patent: Nov. 14, 2017

(54) PASSIVE BENDING SECTION FOR ENDOSCOPE, AND ENDOSCOPE

(71) Applicant: OLYMPUS CORPORATION, Hachioji-shi, Tokyo (JP)

(72) Inventors: Kenichiro Saito, Tachikawa (JP); Takahiro Kishi, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/150,965

(22) Filed: May 10, 2016

(65) Prior Publication Data

US 2016/0249786 A1    Sep. 1, 2016

Related U.S. Application Data

(63) Continuation of application No. PCT/JP2014/081595, filed on Nov. 28, 2014.

(30) Foreign Application Priority Data

Dec. 6, 2013  (JP) ................................. 2013-253475

(51) Int. Cl.
*A61B 1/00* (2006.01)
*A61B 1/005* (2006.01)
*G02B 23/24* (2006.01)
*A61M 25/00* (2006.01)
*A61M 25/01* (2006.01)

(52) U.S. Cl.
CPC .......... *A61B 1/0055* (2013.01); *A61B 1/0057* (2013.01); *A61M 25/0045* (2013.01); *A61M 25/0054* (2013.01); *A61M 25/0138* (2013.01); *G02B 23/2476* (2013.01)

(58) Field of Classification Search
USPC ......................................... 600/139, 141–142
See application file for complete search history.

(56) References Cited

U.S. PATENT DOCUMENTS

| 4,669,172 A | * | 6/1987 | Petruzzi | A61B 1/0055 138/131 |
| 4,805,595 A | * | 2/1989 | Kanbara | A61B 1/00071 600/140 |

(Continued)

FOREIGN PATENT DOCUMENTS

| JP | H09-140660 A | 6/1997 |
| JP | 2006-218231 A | 8/2006 |

(Continued)

OTHER PUBLICATIONS

Mar. 3, 2015 International Search Report issued in International Patent Application No. PCT/JP2014/081595.

(Continued)

*Primary Examiner* — Matthew J Kasztejna
(74) *Attorney, Agent, or Firm* — Oliff PLC

(57) ABSTRACT

A passive bending section for an endoscope is disposed between an active bending section of an inserting section and a flexible tube of the inserting section and is passively bent by receiving an external force. In the passive bending section, a curvature gradually increases from the distal end portion of the passive bending section toward the proximal end portion of the passive bending section.

11 Claims, 14 Drawing Sheets

(56) References Cited

U.S. PATENT DOCUMENTS

| | | | | |
|---|---|---|---|---|
| 4,873,965 A * | 10/1989 | Danieli | A61B 1/0055 138/120 |
| 5,386,816 A * | 2/1995 | Inoue | A61B 1/0055 138/118 |
| 5,488,761 A * | 2/1996 | Leone | A61B 17/164 29/2.1 |
| 5,549,542 A * | 8/1996 | Kovalcheck | A61B 1/0052 600/146 |
| 5,601,599 A * | 2/1997 | Nunez | A61B 10/06 606/205 |
| 6,107,004 A * | 8/2000 | Donadio, III | C23F 1/02 430/320 |
| 6,485,411 B1 * | 11/2002 | Konstorum | A61B 1/0058 600/139 |
| 7,052,489 B2 * | 5/2006 | Griego | A61B 10/04 600/139 |
| 7,591,783 B2 * | 9/2009 | Boulais | A61B 1/00059 600/139 |
| 7,850,604 B2 * | 12/2010 | Wimmer | A61B 1/0055 600/139 |
| 8,075,478 B2 * | 12/2011 | Campos | A61B 1/0008 600/111 |
| 8,317,684 B2 * | 11/2012 | Matsuo | A61B 1/0011 600/125 |
| 2004/0181207 A1 * | 9/2004 | Vitullo | A61M 25/0054 604/523 |
| 2007/0233040 A1 | 10/2007 | Macnamara et al. | |
| 2010/0168519 A1 | 7/2010 | Matsuo | |
| 2013/0144126 A1 | 6/2013 | Iede | |
| 2014/0155697 A1 | 6/2014 | Iede | |

FOREIGN PATENT DOCUMENTS

| | | |
|---|---|---|
| JP | 2006-218232 A | 8/2006 |
| JP | 2009-532085 A | 9/2009 |
| JP | 2012-120573 A | 6/2012 |
| JP | 2013-097327 A | 5/2013 |
| WO | 2012/026231 A1 | 3/2012 |

OTHER PUBLICATIONS

Sep. 15, 2015 Office Action issued in Japanese Patent Application No. 2015-529745.

Jun. 16, 2016 International Preliminary Report on Patentability issued in International Application No. PCT/JP2014/081595.

May 2, 2017 Office Action issued in Chinese Patent Application No. 201480066627.5.

* cited by examiner

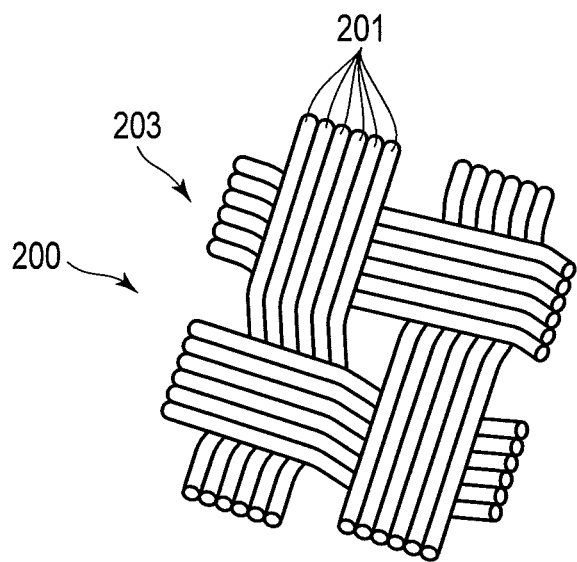
F I G. 3D

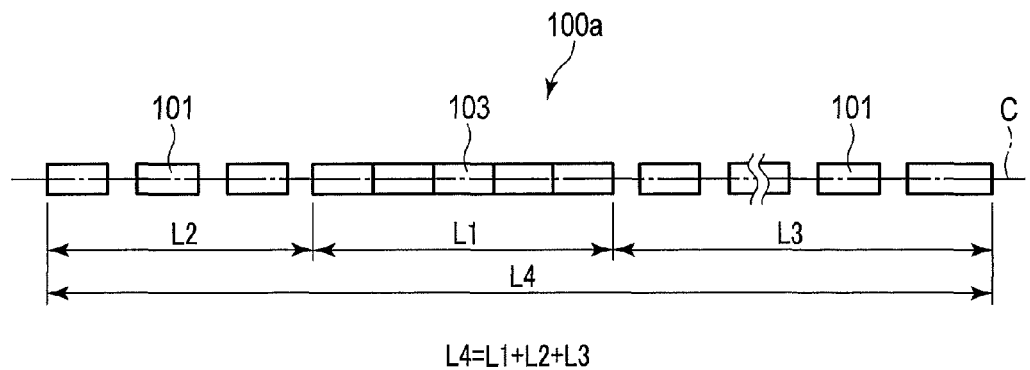
$L4 = L1 + L2 + L3$
F I G. 5C
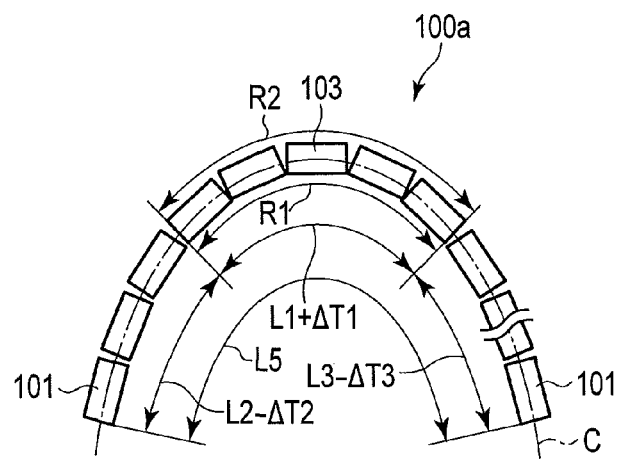
$L5 = L1 + \Delta T1 + L2 - \Delta T2 + L3 - \Delta T3$
$L4 = L5$
$\Delta T1 = \Delta T2 + \Delta T3$
F I G. 5D

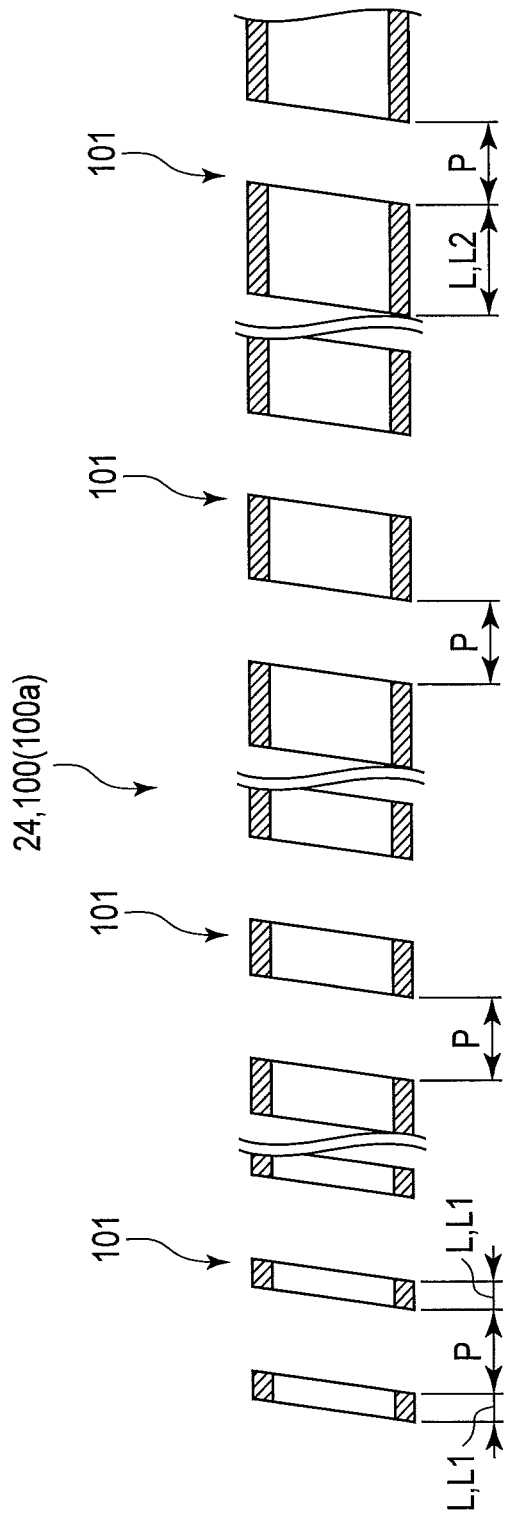

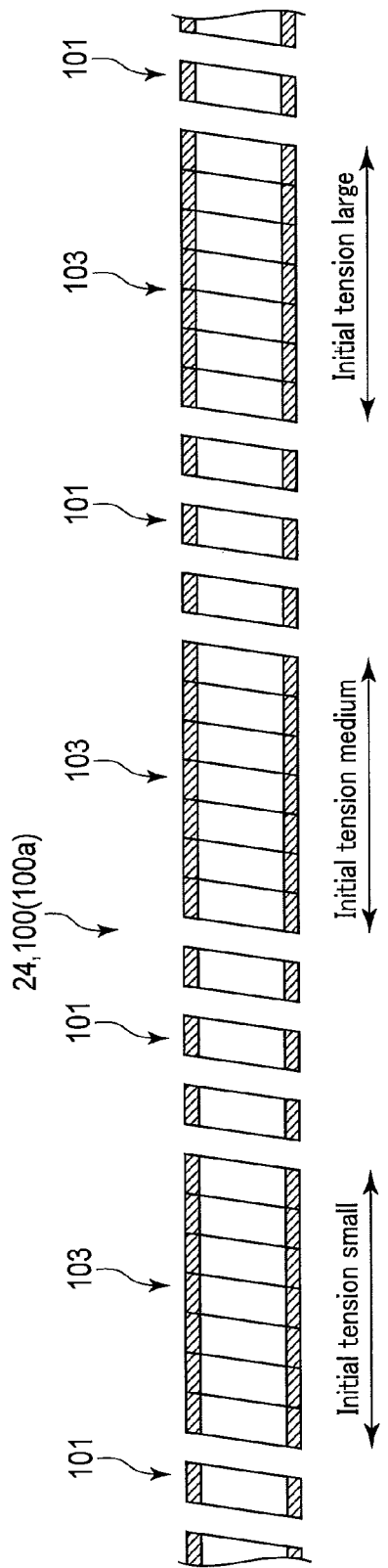
F I G. 6D

PASSIVE BENDING SECTION FOR ENDOSCOPE, AND ENDOSCOPE

CROSS-REFERENCE TO RELATED APPLICATIONS

This application is a Continuation application of PCT Application No. PCT/JP2014/081595, filed Nov. 28, 2014 and based upon and claiming the benefit of priority from prior Japanese Patent Application No. 2013-253475, filed Dec. 6, 2013, the entire contents of all of which are incorporated herein by reference.

BACKGROUND OF THE INVENTION

1. Field of the Invention

The present invention relates to a passive bending section for an endoscope which has a helical tube, and an endoscope having this passive bending section.

2. Description of the Related Art

When an inserting section of an endoscope is inserted into, for example, a lumen, the inserting section needs to smoothly bend from a distal end portion of the inserting section toward a proximal end portion of the inserting section to reduce a patient's pains and improve insertion-removal properties. Such a structure is disclosed in, for example, Jpn. Pat. Appln. KOKAI Publication No. 2006-218232 and Jpn. Pat. Appln. KOKAI Publication No. 2012-120573.

For example, Jpn. Pat. Appln. KOKAI Publication No. 2006-218232 discloses a flexible tube for an endoscope. This flexible tube for the endoscope comprises a bending section, a first flexible tube connected to a proximal end of the bending section, and a second flexible tube connected to a proximal end of the first flexible tube. The first flexible tube has a helical tube, a reticular tube that covers an outer peripheral surface of the helical tube, and an envelope that is made of a resin and covers an outer peripheral surface of the reticular tube. The second flexible tube has a configuration similar to the first flexible tube. The first flexible tube and the second flexible tube are passively bent. A flexural rigidity increases from a distal end of the first flexible tube toward a proximal end of the second flexible tube.

The bending section is constituted by rotatably coupling node rings to one another. In particular, a first bending section is actively bent by a bending operation.

The first flexible tube is a curvature changing section and the second flexible tube is a force amount transfer section. The helical tube of the curvature changing section is integral with the helical tube of the force amount transfer section, and the reticular tube of the curvature changing section is integral with the reticular tube of the force amount transfer section. In the envelope of the curvature changing section, a flexibility of the envelope decreases from a distal end of the envelope toward a proximal end of the envelope. In the envelope of the force amount transfer section, the flexibility of the envelope is constant and equal to the flexibility of the proximal end of the envelope disposed in the curvature changing section.

When the bending section bends to the maximum, a maximum bend radius of the bending section is defined as R1. When a distal end portion of the curvature changing section bends to the maximum, a maximum bend radius of this distal end portion is defined as R2. In this case, R1>R2 is defined. The bend radius of the curvature changing section is gradually increased from a distal end of the curvature changing section toward a proximal end thereof by the abovementioned flexibility of the envelope. In a maximum bend state of the curvature changing section and a maximum bend state of the force amount transfer section, a curvature radius of the curvature changing section is smaller than a curvature radius of the force amount transfer section due to the abovementioned flexibility of the envelope.

When the inserting section bends to the maximum, a bend radius or a curvature of the inserting section changes at a substantially constant ratio due to the abovementioned flexibility of the envelope, and the inserting section smoothly bends from a distal end of the inserting section toward a proximal end thereof. In this way, the smoothness of the bending is acquired.

In general, the flexible tube has the flexibility, and hence the smoothness of the bending is acquired, but the bending is not regulated. Consequently, when the flexible tube abuts on, for example, a wall surface of a lumen, the flexible tube might infinitely be bent by an external force received from the wall surface. The term lumen refers to a region with complex bends as in, for example, a sigmoid colon in a large intestine. In a state where the flexible tube is bent, it is not easy to pass the inserting section including the flexible tube through the bent region. When the flexible tube is inserted into and removed from the lumen, the flexible tube needs to push back the lumen against the force applied from the lumen to the flexible tube.

Thus, for example, in Jpn. Pat. Appln. KOKAI Publication No. 2012-120573, a flexible tube having a helical tube, a reticular tube and an envelope is disclosed. This helical tube has a densely coil and an initial tension is given to the whole densely coil. The flexible tube is not easily bent by the initial tension, and acquires elasticity to push back the lumen. The elasticity have an influence on insertion-removal properties of the flexible tube in a body cavity (in a lumen) of the large intestine or the like. The elasticity include, for example, bouncing properties, a repulsive elasticity, hysteresis, spring properties, a resilience, a flexural rigidity and the like, and have properties to return the bent flexible tube back to a substantially straight state.

BRIEF SUMMARY OF THE INVENTION

An aspect of a passive bending section of the invention is a passive bending section for endoscope, includes a helical tube in which loosely wound portions and densely wound portions to which initial tension is given are alternately disposed along a central axis direction of the helical tube, and a cover that covers an outer peripheral surface of the helical tube so that the cover abuts on the outer peripheral surface of the helical tube, the passive bending section is disposed between an active bending section of an endoscope inserting section and a flexible tube of the endoscope inserting section and being passively bent by receiving an external force, the passive bending section has a distal end portion coupled with the active bending section and a proximal end portion coupled with the flexible tube, and a curvature of the passive bending section gradually increases from the distal end portion toward the proximal end portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3D is an enlarged view of a part of a reticular tube;

FIG. 5C is a schematic view showing relations among a length of the helical tube, a length of a loosely wound portion and a length of the densely wound portion in a linear state of the helical tube;

FIG. 5D is a schematic view showing relations among the length of the helical tube, the length of the loosely wound portion and the length of the densely wound portion in a bent state of the helical tube;

FIG. 6C is a view showing a third modification of the passive bending section;

FIG. 6D is a view showing a fourth modification of the passive bending section;

DETAILED DESCRIPTION OF THE INVENTION

Figure 1:
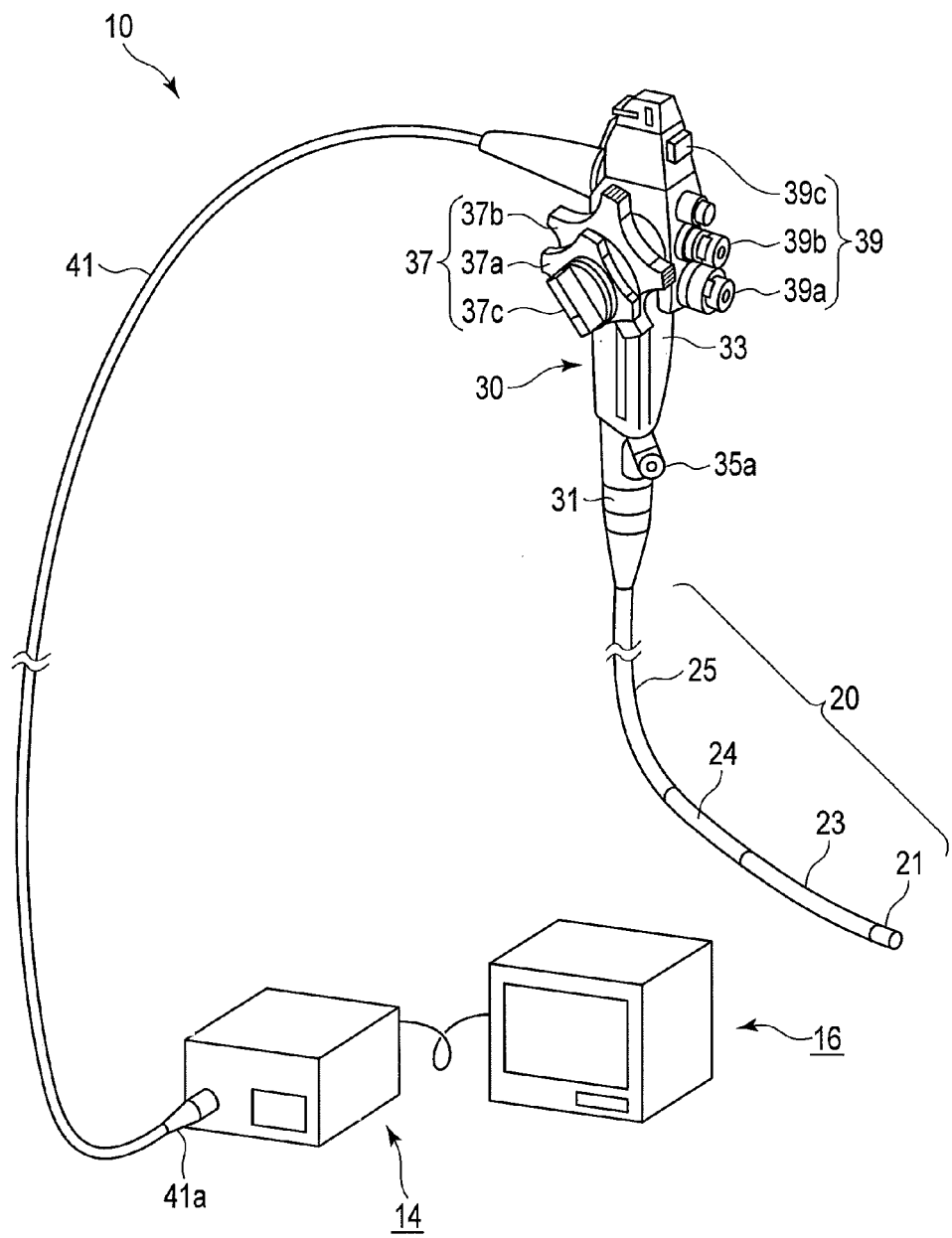
FIG. 1 is a schematic view of an endoscope according to the present invention.

Hereinafter, embodiments of the present invention will be described in detail with reference to the drawings.

First Embodiment

[Configuration]

A first embodiment will be described with reference to FIG. 1, FIG. 2A, FIG. 2B, FIG. 3A, FIG. 3B, FIG. 3C, FIG. 3D, and FIG. 4.

It is to be noted that in parts of the drawings, parts of members are omitted or simplified for clarification of the drawing.

[Endoscope 10]

As shown in FIG. 1, an endoscope 10 has a hollow elongated inserting section 20 which is inserted into a lumen such as a body cavity, and an operating section 30 which is coupled with a proximal end portion of the inserting section 20 and operates the endoscope 10.

[Inserting Section 20]

The inserting section 20 has a distal end hard section 21, an active bending section 23, a passive bending section 24, and a flexible tube 25 from a distal end portion side of the inserting section 20 toward a proximal end portion side of the inserting section 20. A proximal end portion of the distal end hard section 21 is coupled with a distal end portion of the active bending section 23, a proximal end portion of the active bending section 23 is coupled with a distal end portion of the passive bending section 24, and a proximal end portion of the passive bending section 24 is coupled with a distal end portion of the flexible tube 25. The distal end hard section 21, the active bending section 23, the passive bending section 24 and the flexible tube 25 are disposed along a central axis C of the inserting section 20.

The inserting section 20 has a length of, for example, 1300 mm to 1700 mm. The active bending section 23 has a length of, for example, 70 mm to 80 mm. The passive bending section 24 has a length of, for example, 40 mm to 50 mm.

[Distal End Hard Section 21]

The distal end hard section 21 is a distal end portion of the inserting section 20, and is hard and does not bend. The distal end hard section 21 has a main body portion (not shown) made of, for example, a stainless steel material or the like, and a cover that covers an outer periphery of the main body portion. The main body portion is, for example, hard and columnar. The cover is formed into a tubular shape and has insulating properties.

[Active Bending Section 23]

The active bending section 23 is actively bent in a desirable direction such as an upward, downward, right or left direction by an operation of an after-mentioned bending operation portion 37. The active bending section 23 bends, whereby a position and an orientation of the distal end hard section 21 change, an observation object is illuminated with unshown illumination light, and the observation object is captured in an observation viewing field. This observation object is, for example, an affected area, a lesioned area or the like in the subject (e.g., the body cavity).

Figure 2A:
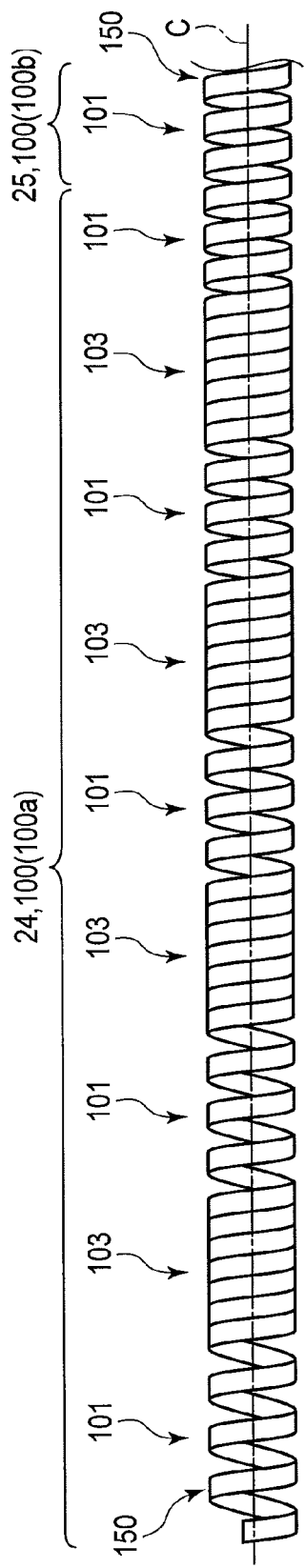
FIG. 2A is a view schematically showing a configuration of a helical tube of a passive bending section and a helical tube of a flexible tube.
Figure 2B:
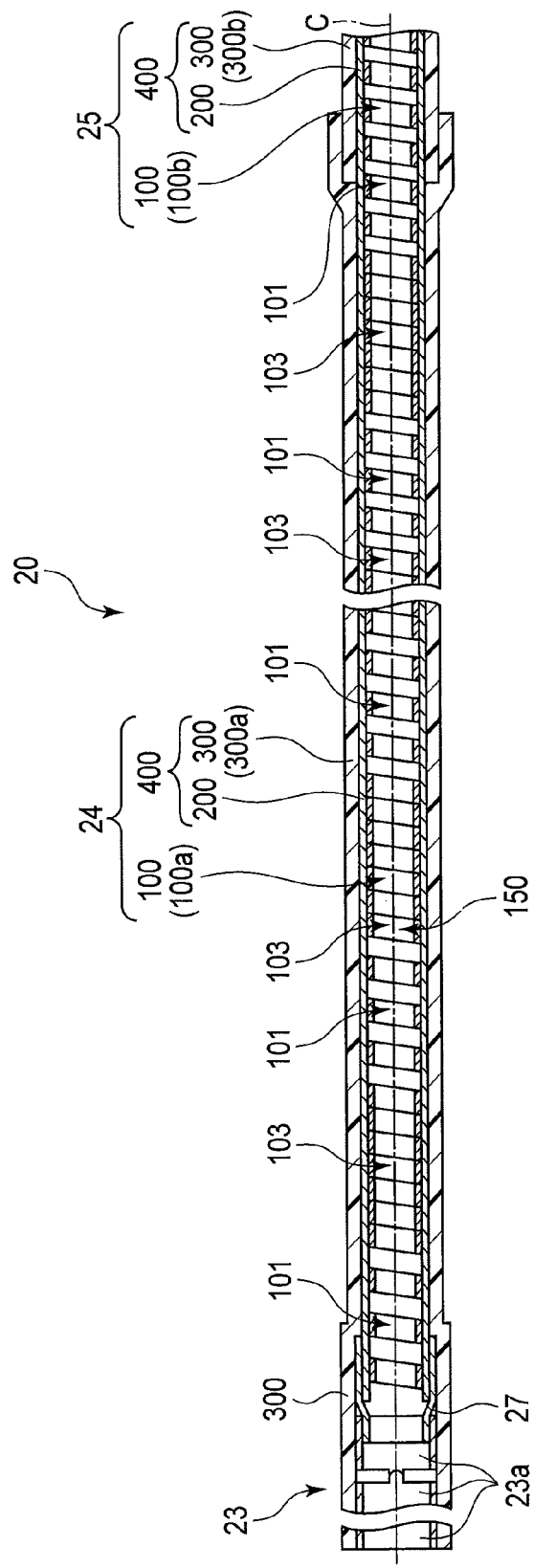
FIG. 2B is a schematically longitudinal cross-sectional view showing a coupling structure of an active bending section, the passive bending section and the flexible tube.

As shown in FIG. 2B, the active bending section 23 has, for example, substantially cylindrical (annular) node rings 23a. The node rings 23a are arranged in parallel along a direction of the central axis C of the inserting section 20, and the node rings 23a adjacent to each other are rotatably coupled with each other, whereby the active bending section 23 is constituted to be bendable (rotatable). The node rings 23a adjacent to each other (positioned forward and backward along the central axis C direction of the inserting section 20) are rotatably coupled with each other by an unshown coupling member such as a pin.

Each node ring 23a has an unshown holding member which is disposed on an inner peripheral surface of the node ring 23a and into which an unshown bending wire is inserted to hold the bending wire. The holding member has, for example, a cylindrical shape. The holding member is fixed to the inner peripheral surface of the node ring 23a by, for example, welding. Two or four holding members are disposed and the holding members are separated from each other by as much as 180° or 90° in a peripheral direction of the node ring 23a. The respective holding members disposed in the node rings 23a are disposed on the same straight line in a longitudinal axis direction of the active bending section 23.

A distal end portion of the bending wire is connected to, for example, the distal end hard section 21 or the node ring 23a disposed at the most distal end of the active bending section 23, i.e., the node ring 23a disposed on a side close to the distal end hard section 21. The bending wire is inserted into the active bending section 23, the passive bending section 24, the flexible tube 25 and a main body section 31. A proximal end portion of the bending wire is connected to the bending operation portion 37. The bending operation portion 37 is operated and the bending wire is pulled, whereby the active bending section 23 bends.

It is to be noted that the node ring 23a disposed in the distal end portion of the active bending section 23 is coupled with the distal end hard section 21 via a coupling member such as an unshown mouthpiece. As shown in FIG. 2B, the node ring 23a disposed in the proximal end portion of the active bending section 23 is coupled with the distal end portion of the passive bending section 24 via a coupling member 27 such as the mouthpiece.

[Passive Bending Section 24]

The passive bending section 24 is disposed between the active bending section 23 and the flexible tube 25 in the central axis C direction of the inserting section 20. The passive bending section 24 has the distal end portion coupled with the proximal end portion of the active bending section 23 via the coupling member 27, and the proximal end portion coupled with the distal end portion of the flexible tube 25.

The passive bending section 24 has a desirable flexibility. Therefore, the passive bending section 24 is passively bent by receiving an external force F. The external force F refers to a force applied to the passive bending section 24 at a desirable angle to a central axis of the passive bending section 24 (the central axis C of the inserting section 20). A configuration of the passive bending section 24 will be described later.

[Flexible Tube 25]

The flexible tube 25 has a desirable flexibility. Therefore, the flexible tube 25 is passively bent by receiving the external force F. The external force F refers to a force to be applied to the flexible tube 25 at a desirable angle to a central axis of the flexible tube 25 (the central axis C of the inserting section 20). The flexible tube 25 is a tubular member extended from the main body section 31 which will be described later in the operating section 30. A configuration of the flexible tube 25 will be described later.

[Operating Section 30]

As shown in FIG. 1, the operating section 30 has the main body section 31 from which the flexible tube 25 is extended, a grasping section 33 that is coupled with a proximal end portion of the main body section 31 and is grasped by an operator who operates the endoscope 10, and a universal cord 41 connected to the grasping section 33.

[Main Body Section 31]

The main body section 31 has a treatment instrument insertion port 35a. The treatment instrument insertion port 35a is coupled with a proximal end portion of an unshown treatment instrument insertion channel. The treatment instrument insertion channel is disposed inside the inserting section 20 and disposed from the flexible tube 25 to the distal end hard section 21. A distal end portion of the treatment instrument insertion channel communicates with an unshown distal end opening portion disposed in the distal end hard section 21. The treatment instrument insertion port 35a is an insertion port through which an unshown treatment instrument for the endoscope is inserted into the treatment instrument insertion channel. The unshown treatment instrument for the endoscope is inserted from the treatment instrument insertion port 35a into the treatment instrument insertion channel, and pushed toward a distal end hard section 21 side. Further, the treatment instrument for the endoscope is projected from the distal end opening portion.

[Grasping Section 33]

The grasping section 33 has the bending operation portion 37 that bends and operates the active bending section 23, and a switch portion 39.

[Bending Operation Portion 37]

The bending operation portion 37 has a right/left bending operation knob 37a that bends and operates the active bending section 23 to right and left by use of the bending wire, an upward/downward bending operation knob 37b that bends and operates the active bending section 23 upward and downward by use of the bending wire, and a fixing knob 37c that fixes a position of the bent active bending section 23.

[Switch Portion 39]

The switch portion 39 has a suction switch 39a, a gas sending/water sending switch 39b, and various switches 39c for endoscope photography. The suction switch 39a, the gas sending/water sending switch 39b and the various switches 39c are operated by operator's hand when the grasping section 33 is grasped by the operator.

The suction switch 39a is operated to make the endoscope 10 suck mucus, fluid or the like from the abovementioned distal end opening portion that also serves as a suction opening portion via the treatment instrument insertion channel that also serves as a suction channel.

For the purpose of acquiring an observation viewing field of an unshown imaging unit in the distal end hard section 21, the gas sending/water sending switch 39b is operated when the fluid is sent from an unshown gas sending tube and an unshown gas sending/water sending tube, and when the fluid is sent from the unshown water sending tube and the gas sending/water sending tube. The fluid includes water or a gas.

The gas sending tube, the water sending tube and the gas sending/water sending tube are disposed from the inserting section 20 via the main body section 31 and the grasping section 33 to the universal cord 41 inside the endoscope 10.

[Universal Cord 41]

The universal cord 41 has a connecting connector 41a that is attachable to and detachable from a control device 14. The control device 14 controls the endoscope 10. The control device 14 has an image processing section that processes an image imaged by the imaging unit. The control device 14 is connected to a display section 16 that displays the image imaged by the imaging unit.

[Relations Among Active Bending Section 23, Passive Bending Section 24 and Flexible Tube 25]

The active bending section 23 is mainly constituted of the node rings 23a as described above.

On the other hand, as shown in FIG. 2A and FIG. 2B, the passive bending section 24 is not constituted of the node rings 23a, but is mainly constituted of a helical tube 100a which will be described later in detail. In this way, the passive bending section 24 is a separate section from the active bending section 23.

As shown in FIG. 2A and FIG. 2B, the flexible tube 25, which will be described later in detail, is mainly constituted of a helical tube 100b substantially similar to the helical tube 100a in about the same manner as in the passive bending section 24.

As shown in FIG. 2A and FIG. 2B, the helical tube 100a of the passive bending section 24 and the helical tube 100b of the flexible tube 25 are integrally formed by one identical helical thin plate member 150. A distal end portion of the thin plate member 150 functions as the helical tube 100a of the passive bending section 24, and a proximal end portion of the thin plate member 150 functions as the helical tube 100b of the flexible tube 25. In this way, the helical tube 100a of the passive bending section 24 and the helical tube 100b of the flexible tube 25 are identical to each other, connected to each other, and integral with each other. Therefore, the passive bending section 24 can function as the distal end portion of the flexible tube 25.

It is to be noted that the helical tube 100a of the passive bending section 24 and the helical tube 100b of the flexible tube 25 may be formed by separate thin plate members 150, respectively, as long as the helical tube of the passive bending section is integrally connected to the helical tube 100b of the flexible tube 25.

In this way, the helical tube 100a of the passive bending section 24 may be continuous with the helical tube 100b of the flexible tube 25.

[Common Configuration of Passive Bending Section 24 and Flexible Tube 25]

Hereinafter, a common configuration of the passive bending section 24 and the flexible tube 25 will be described with reference to FIG. 2A and FIG. 2B in accordance with the passive bending section 24 defined as an example.

As shown in FIG. 2A and FIG. 2B, the passive bending section 24 has, for example, a hollow shape. As shown in FIG. 2A and FIG. 2B, the passive bending section 24 has, for example, a helical tube 100, a reticular tube 200 that covers an outer peripheral surface of the helical tube 100 so that the reticular tube 200 abuts on the outer peripheral surface of the helical tube 100, and an envelope 300 that covers an outer peripheral surface of the reticular tube 200 so that the envelope 300 abuts on the outer peripheral surface of the reticular tube 200. The reticular tube 200 is laminated on the helical tube 100 and the envelope 300 is laminated on the reticular tube 200.

In this way, the passive bending section 24 is constituted of the helical tube 100, the reticular tube 200 and the envelope 300, and consequently, the passive bending section 24 has a three-layer structure by those.

It is to be noted that the reticular tube 200 does not necessarily have to be disposed. Therefore, the passive bending section 24 may be constituted of at least the helical tube 100 and the envelope 300, and consequently, the passive bending section 24 may have a two-layer structure by those.

Therefore, the passive bending section 24 may have the helical tube 100, and a cover 400 that covers the outer peripheral surface of the helical tube 100 so that the cover 400 abuts on the outer peripheral surface of the helical tube 100. The cover 400 has, for example, at least the envelope 300.

[Helical Tube 100]

The helical tube 100 of the present embodiment has desirable elasticity. The term elasticity refers to, for example, a difficulty in bending when the external force is applied the helical tube 100 from a direction away from the central axis C of the inserting section 20 (e.g., a direction orthogonal to the central axis C), and properties to return the bent helical tube 100 to a substantially original straight state.

As shown in FIG. 2A and FIG. 2B, the helical tube 100 is formed by helically winding, for example, the band-like thin plate member 150. That is, the helical tube 100 is a helical elastic tube member having the elasticity. Further, the helical tube 100 is formed into a coil pipe shape. It is to be noted that the thin plate member 150 itself has a rectangular shape and is a thin elongated flat plate member. The thin plate member 150 is made of, for example, a stainless steel material or the like.

Figure 3A:
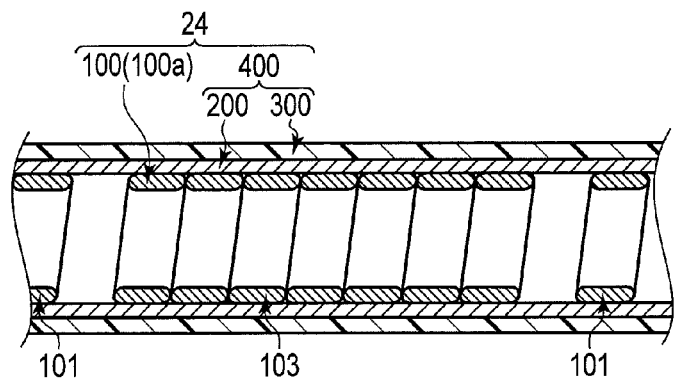
FIG. 3A is a longitudinal cross-sectional view showing a three-layer structure of the passive bending section in a state where a thin plate member of the helical tube has an elongated circular cross section.
Figure 3B:
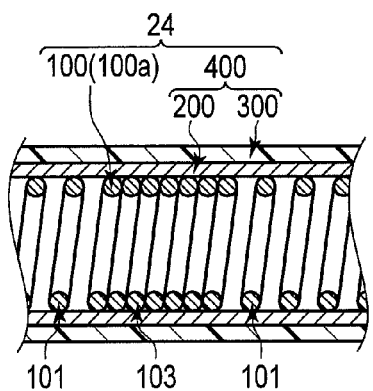
FIG. 3B is a longitudinal cross-sectional view showing the three-layer structure of the passive bending section in a state where the thin plate member of the helical tube has a circular cross section.
Figure 3C:
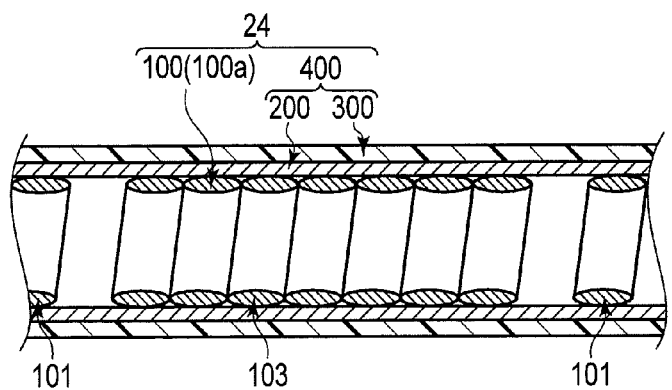
FIG. 3C is a longitudinal cross-sectional view showing the three-layer structure of the passive bending section in a state where the thin plate member of the helical tube has an elliptic cross section.

The transverse cross section of the thin plate member 150 can take any of various shapes; for example, a rectangular shape shown in FIG. 2B, an elongated circular shape shown in FIG. 3A, a substantially circular shape shown in FIG. 3B, an elliptic shape shown in FIG. 3C and the like. Hereinafter, description will be made based on the transverse cross section having a rectangular shape shown in FIG. 2A in this embodiment.

As described above and as shown in FIG. 2A and FIG. 2B, the helical tube 100 of the passive bending section 24 and the helical tube 100 of the flexible tube 25 are not separate from each other but are identical to each other. In this way, one helical tube 100 is shared by the passive bending section 24 and the flexible tube 25. That is, the helical tube 100 is continuously and integrally disposed in the passive bending section 24 and the flexible tube 25.

It is to be noted that as described later, a structure of the helical tube 100 of the passive bending section 24 and a structure of the helical tube 100 of the flexible tube 25 are different from each other in detail. Therefore, hereinafter, for the sake of convenience, the helical tube 100 of the passive bending section 24 will be referred to as the helical tube 100a as described above, and the helical tube 100 of the flexible tube 25 will be referred to as the helical tube 100b as described above.

[Reticular Tube 200]

As shown in FIG. 3D, the reticular tube 200 is formed by braiding, for example, a strand bundle 203 in which strands 201 made of a stainless steel material are bundled, into a substantially circular tube shape. In the reticular tube 200, the strand bundles 203 intersect with one another in the form of a lattice.

It is to be noted that, as shown in FIG. 2B, the reticular tube 200 that covers the helical tube 100a and the reticular tube 200 that covers the helical tube 100b are not separate from each other, but are identical to each other, and integral with each other. In other words, the reticular tube 200 that covers the helical tube 100a is extended from the passive bending section 24 to the flexible tube 25, and covers the helical tube 100b. In this way, the helical tube 100b and the helical tube 100a are covered by one common reticular tube 200. That is, the one reticular tube 200 is shared by the passive bending section 24 and the flexible tube 25. In other words, the reticular tube 200 is continuously and integrally disposed in the passive bending section 24 and the flexible tube 25.

It is to be noted that the reticular tube 200 of the passive bending section 24 may be a separate section from the reticular tube 200 of the flexible tube 25, as long as the reticular tube is integrally connected to the reticular tube 200 of the flexible tube 25.

In this way, the reticular tube 200 of the passive bending section 24 may be continuous with the reticular tube 200 of the flexible tube 25.

For example, the reticular tube 200 that covers the helical tube 100b is harder than the reticular tube 200 that covers the helical tube 100a. This hardness is adjusted by adjusting an intersecting angle between the strand bundles 203.

Respective materials of the reticular tube 200 that covers the helical tube 100a and the reticular tube 200 that covers the helical tube 100b may be identical or different. When the materials are different, each hardness can be adjusted as described above.

[Envelope 300]

The envelope 300 is formed into a substantially circular tube shape to cover the outer peripheral surface of the reticular tube 200.

It is to be noted that, although description will be made later, a structure of the envelope 300 of the passive bending section 24 and a structure of the envelope 300 of the flexible tube 25 are different from each other in detail. Therefore, hereinafter, for the sake of convenience, the envelope 300 of the passive bending section 24 will be referred to as an envelope 300a and the envelope 300 of the flexible tube 25 will be referred to as an envelope 300b. The envelope 300a is a separate portion from the envelope 300b.

[Configuration of Envelope 300a of Peculiar Portion of Passive Bending Section 24]

As shown in FIG. 2B, the envelope 300a is made of a material such as a rubber or a resin, the material has a flexibility. The envelope 300a covers the reticular tube 200 in the passive bending section 24 as described above and also integrally covers the active bending section 23 having the node rings 23a. In detail, the envelope 300a covers the node rings 23a. Therefore, the envelope 300a integrally covers the passive bending section 24 and the active bending section 23.

Consequently, the envelope 300a that covers the reticular tube 200 in the passive bending section 24 is extended from the passive bending section 24 to the active bending section 23, and covers an outer peripheral surface of the active bending section 23 so that the envelope 300a abuts on the outer peripheral surface of the active bending section 23. Further, the reticular tube 200 in the passive bending section 24 and the node rings 23a in the active bending section 23 are covered by one common envelope 300a. That is, the one envelope 300a is shared by the passive bending section 24 and the active bending section 23. In other words, the envelope 300 is continuously and integrally disposed in the passive bending section 24 and the active bending section 23.

It is to be noted that in the envelope 300a, separate envelopes may be joined together, as long as the envelope is continuous and integral with the envelope that covers the active bending section 23.

As shown in FIG. 2B, a boundary portion between the passive bending section 24 and the flexible tube 25 includes, for example, a distal end portion of the helical tube 100b. In this case, a proximal end of the envelope 300a is positioned on a side of, for example, the distal end portion of the helical tube 100b which is the boundary portion, and extended to the flexible tube 25.

[Configuration of Envelope 300b of Peculiar Portion of Flexible Tube 25]

The envelope 300b is made of, for example, two or more types of resin materials. For example, hardnesses of the resin materials are different from each other. The envelope 300 has, for example, a thermoplastic elastomer such as polyurethane or polyester, and a coating layer that coats an outside of this elastomer. The hardness of the envelope 300b is desirably adjusted by changing, for example, blend amounts of the resin materials. The envelope 300b may be made of a resin material such as a rubber material, the resin material has flexible properties. The envelope 300b is made of a resin different from that of the envelope 300a, and is harder than the envelope 300a.

As shown in FIG. 2B, a distal end of the envelope 300b is positioned on the side of the distal end portion of the helical tube 100b. As regards a positional relation between the envelope 300a and the envelope 300b, the proximal end of the envelope 300a covers the distal end of the envelope 300b so that an inner peripheral surface of the proximal end of the envelope 300a abuts on an outer peripheral surface of the distal end of the envelope 300b. Further, the proximal end of the envelope 300a is superimposed on the distal end of the envelope 300b.

[Configuration of Helical Tube 100b of Peculiar Portion of Flexible Tube 25]

As shown in FIG. 2A and FIG. 2B, the helical tube 100b includes, for example, loosely wound portions 101. Consequently, the loosely wound portions 101 are formed by disposing the thin plate members 150 away from each other in an axial direction of the helical tube 100b so that clearance portions are disposed in the axial direction of the helical tube 100b. That is, in the helical tube 100b, the thin plate members 150 do not come in contact closely with each other in the axial direction of the helical tube 100b. In the central axis C direction of the inserting section 20, lengths of the clearance portions are, for example, uniform.

The loosely wound portion 101 of the helical tube 100b is formed like, for example, a coil spring.

As described above, the helical tube 100b has the elasticity. Consequently, the loosely wound portion 101 has the elasticity.

A flexural rigidity of the helical tube 100b is smaller than a flexural rigidity of the helical tube 100a. Therefore, in a case where an external force applied to the passive bending section 24 is equal to an external force applied to the flexible tube 25, the passive bending section 24 bends larger than the flexible tube 25.

[Configuration of Helical Tube 100a of Peculiar Portion of Passive Bending Section 24]

As shown in FIG. 2A and FIG. 2B, the helical tube 100a has the loosely wound portions 101 and densely wound portions 103 to which initial tension is given along the central axis C direction. Each of the densely wound portions 103 has a distal end portion and a proximal end portion; the distal end portion is integrally connected to one loosely wound portion 101, and the proximal end portion is integrally connected to the other loosely wound portion 101. Further, the helical tube 100a alternately has the loosely wound portion 101, the densely wound portion 103 and the loosely wound portion 101 in order from a distal end of the helical tube 100a toward a proximal end of the helical tube 100a. Therefore, the densely wound portion 103 is sandwiched between the loosely wound portions 101 along the central axis C of the helical tube 100a, and the distal end portion of the densely wound portion 103 and the proximal end portion of the densely wound portion 103 are adjacent to the loosely wound portions 101, respectively.

The loosely wound portions 101 are disposed in a distal end portion of the helical tube 100a and a proximal end portion of the helical tube 100a. The loosely wound portion 101 disposed in the distal end portion of the helical tube 100a is coupled with the active bending section 23 via the coupling member 27. The loosely wound portion 101 disposed in the proximal end portion of the helical tube 100a is integrally connected to the loosely wound portion 101 of the flexible tube 25. In consequence, as described above, the helical tube 100a of the passive bending section 24 and the helical tube 100b of the flexible tube 25 are integrated.

The loosely wound portions 101 and the densely wound portions 103 are alternately disposed along the central axis C direction of the helical tube 100a. When this configuration is achieved, there are no special restrictions on the number of the loosely wound portions 101 and the number of the densely wound portions 103. Consequently, in the present embodiment, the densely wound portions 103 are disposed at positions in the passive bending section 24, and hence the passive bending section 24 can more flexibly bend.

As shown in FIG. 2A and FIG. 2B, the helical tube 100a having the loosely wound portions 101 and the densely wound portions 103 is formed by helically winding the thin plate members 150. The loosely wound portions 101 and the densely wound portions 103 are integrally formed by the same one thin plate member 150.

As shown in FIG. 2A and FIG. 2B, the densely wound portion 103 is formed so that the thin plate members 150 adjacent to each other in an axial direction of the helical tube 100a come in contact closely with each other to eliminate the clearance portion therebetween by the abovementioned initial tension. That is, in the densely wound portion 103, the thin plate members 150 come in contact closely with each other in the axial direction of the helical tube 100a.

On the other hand, as shown in FIG. 2A and FIG. 2B, in the loosely wound portion 101 to which the initial tension is not given, the loosely wound portion 101 is formed by disposing the thin plate members 150 away from each other in the axial direction of the helical tube 100a to dispose the clearance portion between the members in the axial direction of the helical tube 100a. That is, in the loosely wound portion 101, the thin plate members 150 do not come in contact closely with each other in the axial direction of the helical tube 100a. In the central axis C direction of the inserting section 20, the lengths of the clearance portions are, for example, uniform. The length of the clearance portion in the helical tube 100a may be equal to or different from the length of the clearance portion in the helical tube 100b.

As described above, the helical tube 100a has the elasticity. Consequently, both of the loosely wound portion 101 and the densely wound portion 103 have the elasticity. However, the elasticity of the densely wound portion 103 are complemented, because the initial tension is given to the densely wound portion 103. Therefore, the elasticity of the densely wound portion 103 are higher than the elasticity of the loosely wound portion 101. Consequently, as to the elasticity of the densely wound portion 103, bouncing properties are strong due to the initial tension as compared with the loosely wound portion 101. In other words, the elasticity of the loosely wound portion 101 are lower than the elasticity of the densely wound portion 103, because the initial tension is not given to the loosely wound portion 101. Therefore, as to the elasticity of the loosely wound portion 101, the bouncing properties are weak as compared with the densely wound portion 103. The elasticity of the densely wound portions 103 are, for example, substantially equal to each other. The elasticity of the loosely wound portions 101 are, for example, substantially equal to each other.

The densely wound portion 103 is formed like, for example, a densely wound coil spring and the loosely wound portion 101 is formed like, for example, a loosely wound coil spring. That is, the densely wound portion 103 is formed like, for example, a densely wound coil and the loosely wound portion 101 is formed like, for example, a loosely wound coil.

Each loosely wound portion 101 has a length of, for example, 10 mm to 50 mm, and each densely wound portion 103 has a length of, for example, 25 mm to 50 mm. It is to be noted that the length of the loosely wound portion 101 is determined in accordance with an elongation amount of the densely wound portion 103 when the passive bending section 24 bends.

[Curvature Radius of Passive Bending Section 24 of Peculiar Portion of Passive Bending Section 24]

As shown in FIG. 2B and as described above, the passive bending section 24 has the distal end portion coupled with the active bending section 23 and the proximal end portion coupled with the flexible tube 25. The passive bending section 24 smoothly bends from the distal end portion toward the proximal end portion. Consequently, for example, a curvature radius of the passive bending section 24 gradually increases from the distal end portion of the passive bending section 24 coupled with the active bending section 23 toward the proximal end portion of the passive bending section 24 coupled with the flexible tube 25.

Here, one example of the above configuration will be described below.

Figure 4:
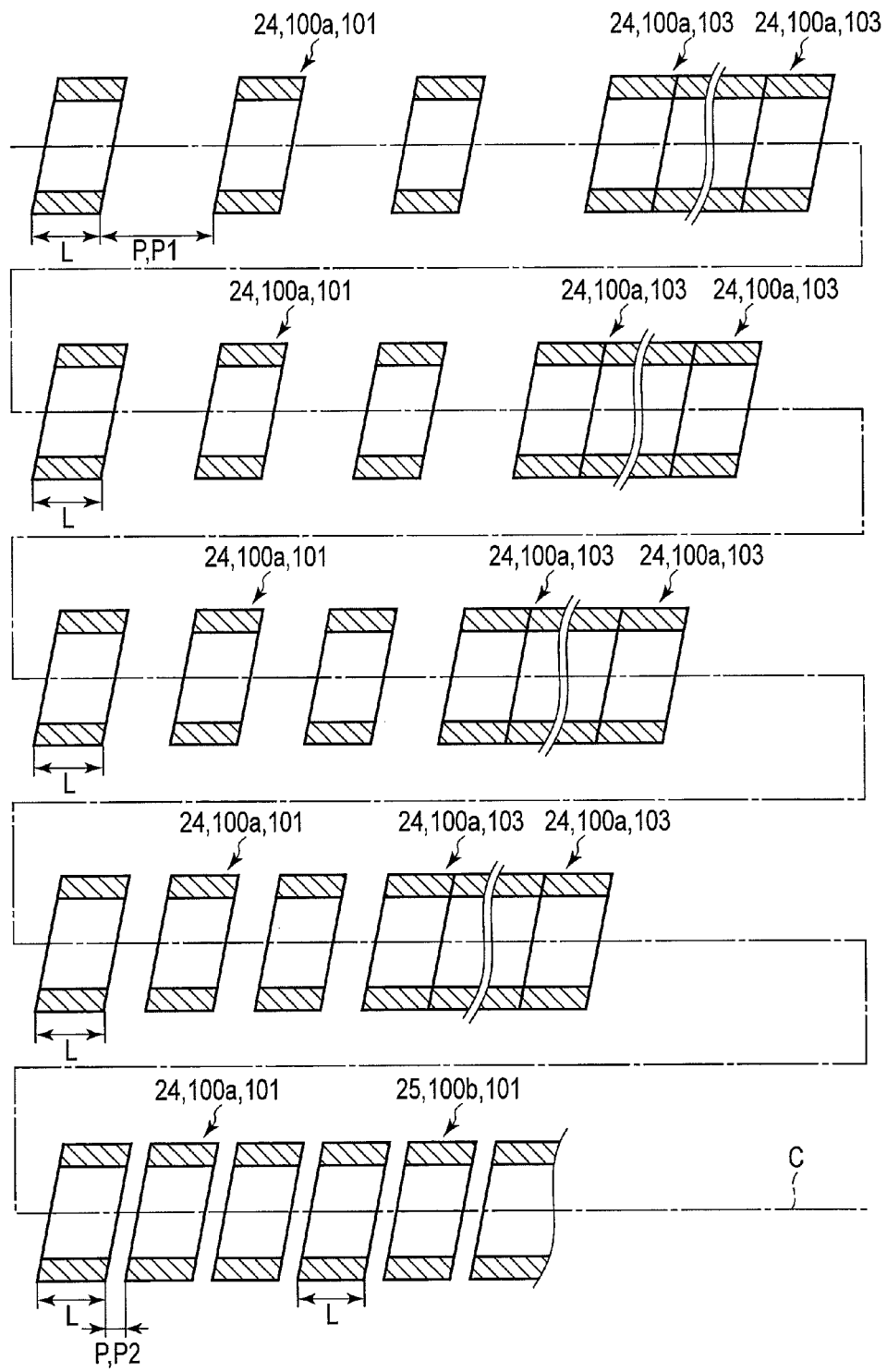
FIG. 4 is a view showing a state where pitches P gradually narrow from a distal end portion of the passive bending section toward a proximal end portion of the passive bending section.

As shown in FIG. 2A, FIG. 2B and FIG. 4, in the thin plate member 150 that is a material forming the loosely wound portion 101 of the passive bending section 24, the pitches P are formed. The pitch P refers to a length in the axial direction of the helical tube 100a. The pitch P also refers to a length of the abovementioned clearance portion. The pitches P gradually narrow from the distal end portion of the passive bending section 24 toward the proximal end portion of the passive bending section 24.

Specifically, as shown in FIG. 4, each of pitches P1 in the loosely wound portion 101 disposed on the active bending section 23 side is larger than each of pitches P2 in the loosely wound portion 101 disposed on the flexible tube 25 side. In this case, a length L of a thin plate is, for example, uniform in a longitudinal direction of the loosely wound portion 101. The length L of the thin plate refers to a width of the band-like thin plate member 150 which is the material forming the loosely wound portion. The respective pitches P in one loosely wound portion 101 are, for example, equal to each other. The numbers of the pitches P are identical to each other in the respective loosely wound portions 101. The numbers of windings of the respective loosely wound portions 101 are, for example, equal to each other. The pitch P has a length of, for example, 2.5 mm to 4 mm.

The lengths of the respective densely wound portions 103 are, for example, uniform, amounts of the initial tension in the respective densely wound portions 103 are, for example, equal to each other, and the numbers of the windings of the respective densely wound portions 103 are, for example, equal to each other.

[Initial Tension]

Here, the initial tension given to the densely wound portion 103 for use in the present embodiment will be described.

Figure 5A:
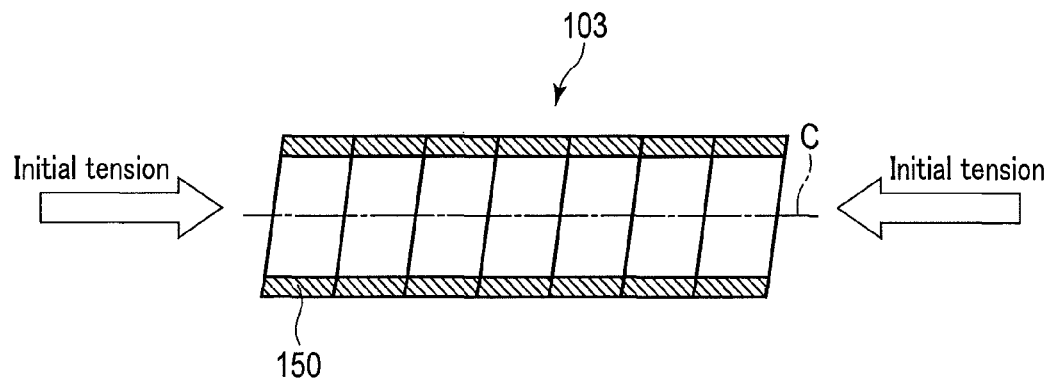
FIG. 5A is a schematic longitudinal cross-sectional view showing a state where an initial tension is given to a densely wound portion of the helical tube to maintain a straight state of the densely wound portion.

As shown in FIG. 5A, the initial tension is a force that acts in a direction in which edge portions of the thin plate members 150 of the densely wound portion 103 are brought into contact closely with each other in the central axis C direction of the densely wound portion 103. In other words, the initial tension is a force (a preload) with which a state where the edge portions of the thin plate members 150 of the densely wound portion 103 are in contact closely with each other is maintained and which the densely wound portion 103 is hard to bend and maintains a substantially linear state against the external force F (e.g., gravity), when the central axis C of the densely wound portion 103 is, for example, horizontally disposed. The initial tension is a force (a preload) with which the state where the edge portions of the thin plate members 150 of the densely wound portion 103 are in contact closely with each other is maintained against gravity and the thin plate members 150 are maintained so that no clearance portion is generated between the thin plate members, when the central axis C of the densely wound portion 103 is, for example, vertically disposed.

Additionally, in particular, when the initial tension is defined as "a force to maintain the state where the edge portions of the thin plate members 150 are in contact closely with each other" as described above and that is given to the whole densely wound portion 103, the force to be applied to each of the edge portions of the adjacent thin plate members 150 and to bring the edge portions into contact closely with each other can be defined as a "close contact force".

Figure 5B:
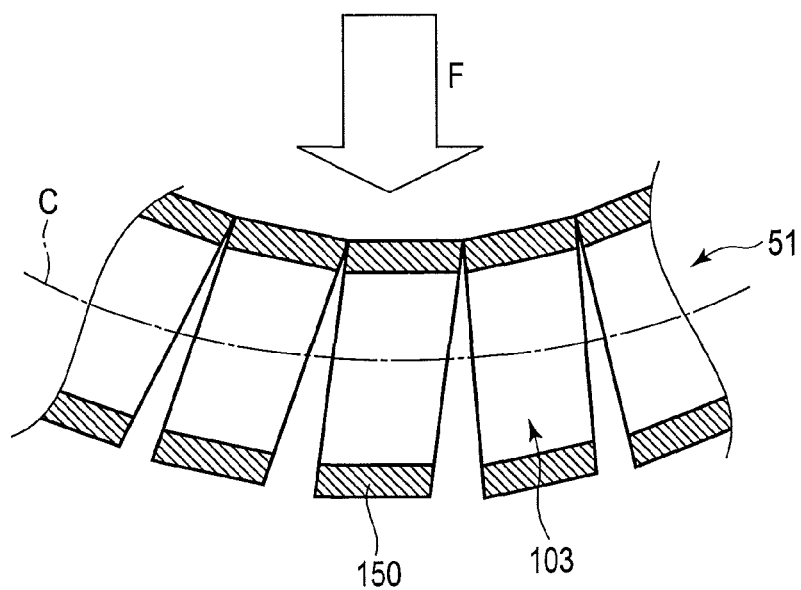
FIG. 5B is a schematic longitudinal cross-sectional view showing a state where the densely wound portion is deformed when a force is applied from a side to a central axis of the densely wound portion.

For example, the external force F is applied toward the central axis C in a state where the central axis C of the densely wound portion 103 is, for example, horizontally disposed as shown in FIG. 5A. At this time, no clearance portion is formed between the thin plate members 150 and no bending occurs in the densely wound portion 103 until the external force F reaches a force to release the close contact force, in other word, until the external force F exceeds the close contact force. On the other hand, when the external force F applied toward the central axis C reaches the force to release the close contact force or more as shown in FIG. 5B, in other word, when the external force F exceeds the close contact force, the clearance portion is formed between the thin plate members 150 which come in contact closely with each other, and the bending occurs in the densely wound portion 103. Therefore, the flexural rigidity of the helical tube 100a is increased by the close contact force applied to the densely wound portion 103 until the densely wound portion 103 starts bending. When the close contact force is released by the external force F and the densely wound portion 103 starts bending, the helical tube 100a bends in accordance with a spring constant which the helical tube 100a has. Therefore, when the inserting section 20 is inserted into a body cavity (into a lumen) of, for example, a large intestine or the like and bending of the densely wound portion 103 is started, the passive bending section 24 can be bent in such a state that the densely wound portion 103 is not present.

Such initial tension is given to the densely wound portion 103 when the helical tube 100a is formed, i.e., when the densely wound portion 103 is manufactured. The initial tension to be given at this time can suitably be adjusted in accordance with, for example, a winding degree of the thin plate member 150.

Here, a length of the cylindrical envelope 300 in the axial direction along the central axis C is substantially unchanged and about the same even in a linear state or a bent state of the envelope 300. Therefore, a length of the central axis C of the helical tube 100a covered with the envelope 300 is also substantially unchanged and about the same even in a linear state or a bent state of the helical tube 100a. Consequently, as shown in FIG. 5B, also when the external force F is received from a direction away from the central axis C of the passive bending section 24, the total length of the helical tube 100a hardly changes.

As shown in FIG. 5C, in the axial direction of the helical tube 100a in the linear state, a length of the densely wound portion 103 in a direction along the central axis C is defined as L1, a length of one loosely wound portion 101 in the direction along the central axis C is defined as L2, a length of the other loosely wound portion 101 in the direction along the central axis C is defined as L3, and a length of the central axis C of the helical tube 100a in the direction along the central axis C is defined as L4. At this time, the following equation is established:

$$L4 = L1 + L2 + L3 \qquad \text{Equation (1).}$$

The external force F is applied to the helical tube 100a in a state shown in FIG. 5C from a direction away from the central axis C of the helical tube 100a and the helical tube 100a is bent as shown in FIG. 5D. As shown in FIG. 5D, the thin plate members 150 of an inner circular part R1 maintain an abutting state on each other due to the initial tension to the central axis C of the densely wound portion 103, and the thin plate members 150 of an outer circular part R2 detach away from each other to the central axis C of the densely wound portion 103. Consequently, the entire length of the central axis C of the densely wound portion 103 elongates by as much as ΔT1. That is, in a case where the densely wound portion 103 is bent, the length of the central axis C of the densely wound portion 103 in the axial direction is L1+ΔT1.

When the length of the central axis C of the densely wound portion 103 in the axial direction in a linear state of the densely wound portion 103 (see FIG. 5C) is compared with the length in a bent state of the densely wound portion (see FIG. 5D), the latter length is longer by as much as ΔT1. Further, in the present embodiment, the loosely wound portions 101 are disposed to sandwich the densely wound portion 103 therebetween.

Consequently, as shown in FIG. 5C and FIG. 5D, when the densely wound portion 103 is bent, the edge portions of the thin plate members 150 in the direction along the central axis C of the loosely wound portion 101 on a distal end side come close to each other as compared with a case where the distal end side (one) loosely wound portion 101 is in the linear state. That is, when the densely wound portion 103 is bent, the clearance portion between the edge portions of the thin plate members 150 narrows in the distal end side loosely wound portion 101. Consequently, the length of the distal end side loosely wound portion 101 in the axial direction along the central axis C contracts by as much as ΔT2 as compared with the case where the loosely wound portion 101 is in the linear state. That is, when the densely wound portion 103 is bent, the length of the distal end side loosely wound portion 101 in the axial direction along the central axis C is L2-ΔT2.

As shown in FIG. 5C and FIG. 5D, when the densely wound portion 103 is bent, the edge portions of the thin plate members 150 in the direction along the central axis C of the loosely wound portion 101 on a proximal end side come close to each other as compared with a case where the proximal end side (other) loosely wound portion 101 is in the linear state. That is, when the densely wound portion 103 is bent, the clearance portion between the edge portions of the thin plate members 150 narrows in the proximal end side loosely wound portion 101. Consequently, the length of the proximal end side loosely wound portion 101 in the axial direction along the central axis C contracts by as much as ΔT3 as compared with the case where the loosely wound portion 101 is in the linear state. That is, when the densely wound portion 103 is bent, the length of the proximal side loosely wound portion 101 in the axial direction along the central axis C is L3-ΔT3.

At this time, as shown in FIG. 5D, when a length of the central axis C of the bent helical tube 100a is defined as L5, the following equation is established:

$$L5=L1+\Delta T1+L2-\Delta T2+L3-\Delta T3 \quad \text{Equation (2)}.$$

Here, as described above, the length of the central axis C of the helical tube 100a needs to be unchanged and the same even in the linear state or the bent state of the helical tube 100a. That is, the following equation needs to be established:

$$L4=L5 \quad \text{Equation (3)}.$$

When Equations (1) and (2) mentioned above are substituted into Equation (3), the following equation is obtained:

$$L1+L2+L3=L1+\Delta T1+L2-\Delta T2+L3-\Delta T3, \text{ and}$$

the following equation is established:

$$\Delta T1=\Delta T2+\Delta T3 \quad \text{Equation (4)}.$$

In other words, Equation (4) becomes as follows: Elongation amount of the densely wound portion 103="contraction amount of one loosely wound portion 101"+"contraction amount of the other loosely wound portion 101".

In this way, the elongation amount of the densely wound portion 103 is equal to a contraction amount obtained by adding the contraction amounts of the respective loosely wound portions 101, and the loosely wound portion 101 contracts by as much as the amount by which the densely wound portion 103 elongates. That is, when the passive bending section 24 bends, the loosely wound portion 101 absorbs the elongation of the helical tube 100a in the direction along the central axis C which accompanies the elongation of the densely wound portion 103 in the direction along the central axis C in the axial direction of the helical tube 100a. Therefore, the loosely wound portions 101 offset the elongation of the helical tube 100a in the direction along the central axis C. Thus, the loosely wound portions 101 are present, whereby the passive bending section 24 can smoothly be bent in a state where characteristics of the densely wound portions 103 having high spring properties to the loosely wound portions 101 are maintained.

When the inserting section 20 is inserted into the body cavity (into the lumen) of the large intestine or the like, in general, a user of the endoscope 10 pushes a distal end of the inserting section 20 into the body cavity while holding the grasping section 33 of the operating section 30 with the left hand and holding the passive bending section 24 with the right hand.

When a position of the passive bending section 24 which corresponds to the densely wound portion 103 maintains its linear state and the passive bending section 24 is inserted into the body cavity (into the lumen) of, for example, the large intestine or the like, the external force F (including the gravity) applied to the densely wound portion 103 from a direction (e.g., an orthogonal direction) away from a direction along, for example, the central axis C of the helical tube 100a is smaller than a component of the initial tension in the direction orthogonal to the central axis C. In this case, the densely wound portion 103 does not bend due to high spring properties, maintains its linear state. Consequently, an operation force amount of the passive bending section 24 held by the right hand of the user of the endoscope 10 is transferred from the held position to the distal end portion of the passive bending section 24 (the distal end portion of the helical tube 100a), and the passive bending section 24 is easily inserted into the body cavity. That is, the position which corresponds to the densely wound portion 103 in the passive bending section 24 can maintain the linear state, and be inserted into the lumen without being bent.

In a case where the external force F (including the gravity) applied to the densely wound portion 103 of the passive bending section 24 of the inserting section 20 from the direction (e.g., an orthogonal direction) away from the direction along the central axis C of the densely wound portion is not less than the component of the initial tension in the direction orthogonal to the central axis C, the densely wound portion 103 starts bending against the high spring properties of the densely wound portion 103. When the external force F is applied, a space (the clearance portion) between the thin plate members 150 of the loosely wound portion 101 is decreased.

[Operation]

As shown in FIG. 2A, FIG. 2B and FIG. 4, in the present embodiment, the helical tube 100a has the loosely wound portions 101 and the densely wound portions 103 to which the initial tension is given. The passive bending section 24 has the helical tube 100a. In the passive bending section 24, the pitches P gradually narrow from the distal end portion of the passive bending section 24 toward the proximal end portion of the passive bending section 24. Therefore, the curvature radius of the passive bending section 24 gradually increases from the distal end portion of the passive bending section 24 toward the proximal end portion of the passive bending section 24.

Further, when the passive bending section 24 is inserted into and removed from the body cavity (the inside of the lumen) of a bending large intestine or the like, the passive bending section 24 receives the external force F from a bent region in the body cavity. When the external force is not less than the initial tension, the passive bending section 24 bends.

At this time, according to the abovementioned configuration, the passive bending section 24 smoothly bends from the distal end portion of the passive bending section 24 toward the proximal end portion of the passive bending section 24.

Consequently, in the passive bending section 24, smoothness of the bending of the passive bending section 24 does not depend on the envelope 300a, but depends on the helical tube 100a that is a main portion of the passive bending section 24. In consequence, the smoothness of the bending is sufficiently acquired by the abovementioned configuration, and the elasticity are also sufficiently acquired by the initial tension.

The helical tube 100a has the loosely wound portions 101 and the densely wound portions 103 to which the initial tension is given, and the loosely wound portions 101 and the densely wound portions 103 are alternately arranged. In the loosely wound portion 101, the pitches P are set as described above. Therefore, as compared with a case where the helical tube 100a only has the densely wound portion 103 to which the initial tension is given, the smoothness of the bending is prevented from being deteriorated by the initial tension, and the passive bending section 24 securely and smoothly bends.

Consequently, the passive bending section 24 is easy to be inserted and removed along, for example, the bending large intestine, and the passive bending section 24 is easy to be inserted into and removed from the body cavity. In consequence, insertion-removal properties of the passive bending section 24 improve.

At this time, the passive bending section 24 bends, and hence also when the passive bending section abuts on the large intestine that bends, the large intestine is not strongly pressed, is not put under high tension, and the patient is not unduly burdened as a result.

When the external force F is not applied, the whole passive bending section 24 is returned to the linear state by the densely wound portions 103 having the initial tension.

As described above, in the helical tube 100a, the elasticity of the densely wound portion 103 are strong due to the initial tension, and the elasticity of the loosely wound portion 101 are low. Therefore, when the whole passive bending section 24 receives the external force F from the bent region in the body cavity, the densely wound portion 103 noticeably pushes up (bounces back) the bent region against the external force F and the loosely wound portion 101 pushes up (bounces back) the bent region a little against the external force F. Thus, a pushup force in the densely wound portion 103 is stronger than a pushup force in the loosely wound portion 101 due to the elasticity. Therefore, the pushup force varies in the helical tube 100a, but the helical tube 100a pushes back the bent region with a substantially uniform force in the whole helical tube 100a, and the insertion-removal properties of the passive bending section 24 improve.

As described above, the smoothness of the bending is compatible with the elasticity, and the insertion-removal properties improve.

The elasticity are acquired, and hence when the passive bending section 24 is operated, a shortening operation of bending the whole inserting section 20 by this operation is easily carried out.

The reticular tube 200 of the passive bending section 24 is identical to the reticular tube 200 of the flexible tube 25. In detail, the reticular tube 200 that covers the helical tube 100a is extended from the passive bending section 24 to the flexible tube 25 to cover the helical tube 100b.

Consequently, in the passive bending section 24 and the flexible tube 25, the smoothness of the bending is acquired, the passive bending section 24 and the flexible tube 25 are easily integrally prepared, and assembling properties improve.

The envelope 300a of the passive bending section 24 is extended to the active bending section 23, and covers the outer peripheral surface of the active bending section 23 so that the envelope 300 abuts on the outer peripheral surface of the active bending section 23.

Consequently, the number of components is decreased, and in the active bending section 23 and the passive bending section 24, the smoothness of the bending is acquired, the active bending section 23 and the passive bending section 24 are easily integrally prepared, and the assembling properties improve.

The envelope 300b of the flexible tube 25 is made of a resin different from that of the envelope 300a of the passive bending section 24, and is harder than the envelope 300a. The proximal end of the envelope 300a is superimposed on the distal end of the envelope 300b.

Therefore, in a case where the external force applied to the passive bending section 24 is equal to the external force applied to the flexible tube 25, the passive bending section 24 bends less than the flexible tube 25. Further, the inserting section 20 smoothly bends from the distal end portion of the inserting section 20 toward the proximal end portion of the inserting section 20, specifically from the passive bending section 24 toward the flexible tube 25. The boundary portion between the passive bending section 24 and the flexible tube 25 is easily distinguished, and water tightness is securely acquired in the passive bending section 24 and the flexible tube 25.

The loosely wound portions 101 are disposed in the distal end portion of the passive bending section 24 coupled with the active bending section 23 and the proximal end portion of the passive bending section 24 coupled with the flexible tube 25. This distal end portion functions as a coupling portion of the active bending section 23 with the passive bending section 24, and the proximal end portion functions as a coupling portion of the passive bending section 24 with the flexible tube 25. The loosely wound portion 101 of the passive bending section 24 disposed in the proximal end portion is integrally connected to the loosely wound portion 101 of the flexible tube 25. In the loosely wound portion 101, the pitches P are set as described above.

Therefore, also in these coupling portions, the smoothness of the bending is acquired. As a result, the inserting section 20 smoothly bends from the distal end portion of the inserting section 20 toward the proximal end portion of the inserting section 20, and also in the inserting section 20, the smoothness of the bending is acquired.

The passive bending section 24 does not have the structure of the active bending section 23, but acquires the smoothness of the bending, and it is not necessary to increase the number of structures or the number of components, and the assembling properties improve.

[Effect]

Consequently, in the present embodiment, the helical tube 100a has the loosely wound portions 101 and the densely wound portions 103 to which the initial tension is given. The passive bending section 24 has the helical tube 100a. In the passive bending section 24, the pitches P gradually narrow from the distal end portion of the passive bending section 24 toward the proximal end portion of the passive bending section 24. Therefore, in the present embodiment, the curvature radius of the passive bending section 24 can gradually be increased from the distal end portion of the passive bending section 24 toward the proximal end portion of the passive bending section 24.

As a result, in the present embodiment, the passive bending section 24 can securely and smoothly be bent.

In the present embodiment, the smoothness of the bending of the passive bending section 24 does not depend on the envelope 300a, but depends on the helical tube 100a that is the main portion of the passive bending section 24. Consequently, in the present embodiment, the smoothness of the bending can sufficiently be acquired and the elasticity can also sufficiently be acquired by the initial tension.

In the present embodiment, the helical tube 100a has the loosely wound portions 101 and the densely wound portions 103 to which the initial tension is given, and the loosely wound portions 101 and the densely wound portions 103 are alternately arranged. According to the present embodiment, in the loosely wound portion 101, the pitches P are set as described above. Therefore, in the present embodiment, as compared with the case where the helical tube 100a only has the densely wound portion 103 to which the initial tension is given, the smoothness of the bending can be prevented from being deteriorated by the initial tension, and the passive bending section 24 can securely and smoothly be bent.

In the present embodiment, the passive bending section 24 can be easily inserted and removed along, for example, the bending large intestine and the passive bending section 24 can be easily inserted into and removed from the body cavity. In this way, according to the present embodiment, the insertion-removal properties of the passive bending section 24 can improve.

In the present embodiment, at this time, the passive bending section 24 bends, and hence also when the passive bending section abuts on the large intestine that bends, the large intestine is not strongly pressed, is not put under high tension, and the patient is not unduly burdened as a result.

In the present embodiment, when the external force F is not applied, the whole passive bending section 24 can be returned to the linear state by the densely wound portions 103 having the initial tension.

In the present embodiment, the helical tube 100a can push back the bent region with the substantially uniform force in the whole helical tube 100a, and the insertion-removal properties of the passive bending section 24 can improve.

In the present embodiment, as described above, the smoothness of the bending can be compatible with the elasticity, and the insertion-removal properties can improve. In the present embodiment, the elasticity can be acquired, and hence when the passive bending section 24 is operated, the shortening operation of bending the whole inserting section 20 by this operation can easily be carried out.

In the present embodiment, the reticular tube 200 of the passive bending section 24 is identical to the reticular tube 200 of the flexible tube 25. In detail, the reticular tube 200 that covers the helical tube 100a is extended from the passive bending section 24 to the flexible tube 25 so that the reticular tube 200 covers the helical tube 100b.

Consequently, according to the present embodiment, in the passive bending section 24 and the flexible tube 25, the smoothness of the bending can be acquired, the passive bending section 24 and the flexible tube 25 can easily integrally be prepared, and the assembling properties can improve.

In the present embodiment, the envelope 300a of the passive bending section 24 is extended to the active bending section 23, and covers the outer peripheral surface of the active bending section 23 so that the envelope 300a abuts on the outer peripheral surface of the active bending section 23.

Consequently, in the present embodiment, the number of the components can be decreased, and in the active bending section 23 and the passive bending section 24, the smoothness of the bending can be acquired, the active bending section 23 and the passive bending section 24 can easily integrally be prepared, and the assembling properties can improve.

In the present embodiment, the envelope 300b of the flexible tube 25 is made of a resin different from that of the envelope 300a of the passive bending section 24, and is harder than the envelope 300a. The proximal end of the envelope 300a is superimposed on the distal end of the envelope 300b.

Therefore, according to the present embodiment, in the case where the external force applied to the passive bending section 24 is equal to the external force applied to the flexible tube 25, the passive bending section 24 can be bent less than the flexible tube 25. Further, in the present embodiment, the inserting section 20 can smoothly be bent from the distal end portion of the inserting section 20 toward the proximal end portion of the inserting section 20, specifically from the passive bending section 24 toward the flexible tube 25. In the present embodiment, the boundary portion between the passive bending section 24 and the flexible tube 25 can easily be distinguished, and the water tightness can securely be acquired in the passive bending section 24 and the flexible tube 25.

In the present embodiment, the loosely wound portions 101 are disposed in the distal end portion of the passive bending section 24 and the proximal end portion of the passive bending section 24, which function as the coupling portions. In the present embodiment, the loosely wound portion 101 of the passive bending section 24 disposed in the proximal end portion is integrally connected to the loosely wound portion 101 of the flexible tube 25.

Therefore, in the present embodiment, also in these coupling portions, i.e., the coupling portion of the active bending section 23 with the passive bending section 24 and the coupling portion of the passive bending section 24 with the flexible tube 25, the smoothness of the bending can be acquired. As a result, in the present embodiment, the inserting section 20 can smoothly be bent from the distal end portion of the inserting section 20 toward the proximal end portion of the inserting section 20, and also in the inserting section 20, the smoothness of the bending can be acquired.

In the present embodiment, the passive bending section 24 does not have the structure of the active bending section 23, but in the passive bending section 24, the smoothness of the bending can be acquired, and it is not necessary to increase the number of structures or the number of the components in the passive bending section 24, and the assembling properties of the passive bending section 24 can improve.

In the present embodiment, the reticular tube 200 is shared by the passive bending section 24 and the flexible tube 25, and the envelope 300a is shared by the passive bending section 24 and the active bending section 23. Consequently, in the present embodiment, the inserting section 20 can easily be prepared, and the assembling properties can improve.

It is to be noted that in the present embodiment, the pitches P are uniform in one loosely wound portion 101, but the present invention does not have to be limited to this embodiment. For example, the pitches may gradually narrow from the distal end portion of the loosely wound portion 101 toward the proximal end portion of the loosely wound portion 101 so that the pitches widen on the distal end portion side of the loosely wound portion 101 and narrow on the proximal end portion side of the loosely wound portion 101 in one loosely wound portion 101.

In this case, for example, the pitch P in the proximal end portion of the loosely wound portion 101 disposed on the distal end portion side of the passive bending section 24 is narrower than the pitch P in the distal end portion of the loosely wound portion 101 disposed on the proximal end portion side of the passive bending section 24.

According to the present embodiment, in the flexible tube 25, the whole helical tube 100b may be formed as, for example, the loosely wound portion 101, or does not have to be limited to this embodiment. The helical tube 100b may have at least the loosely wound portion 101. Consequently, in a state where the flexible tube 25 has the loosely wound portion 101, the flexible tube 25 may further have at least one of the densely wound portion 103 to which the initial tension is not given and the densely wound portion 103 to which the initial tension is given.

The helical tube 100a and the helical tube 100b may be separate from each other as described above. The reticular tube 200 of the passive bending section 24 and the reticular tube 200 of the flexible tube 25 may be separate from each other as described above. The envelope 300a of the passive bending section 24 and the envelope of the active bending section 23 may be identical to each other.

Modifications

In the first embodiment, as one example of the curvature radius of the passive bending section 24, the pitches P gradually narrow from the distal end portion of the passive bending section 24 toward the proximal end portion of the passive bending section 24. However, the present invention does not have to be limited to this embodiment. This aspect will be described below as modifications. Hereinafter, configurations different from the configuration of the first embodiment will only be described. It is to be noted that any configuration which is the same as the configuration of the first embodiment is denoted with the same reference signs and detailed description thereof is omitted.

First Modification

Figure 6A:
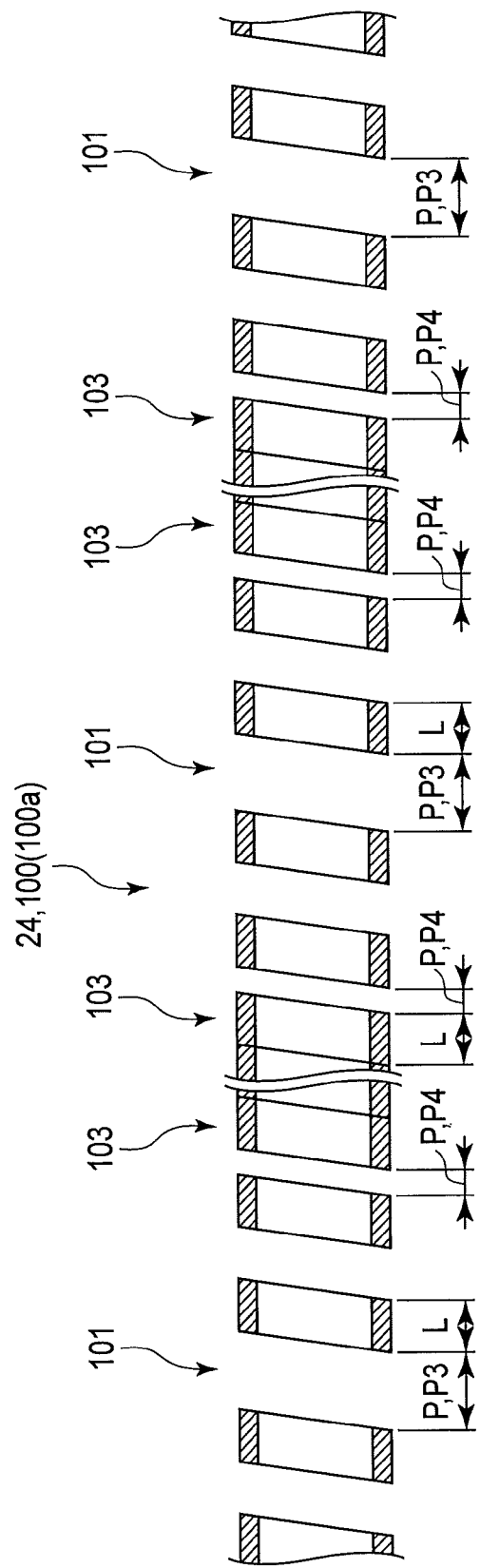
FIG. 6A is a view showing a first modification of the passive bending section.

As shown in FIG. 6A, pitches P gradually narrow with proximity to a densely wound portion 103, and gradually widen with increased distance from the densely wound portion 103. That is, a pitch P3 at a central portion of the loosely wound portion 101 is wide and a pitch P4 at an end portion of a loosely wound portion 101 is narrow.

In this case, lengths L of the respective loosely wound portions 101 are, for example, uniform. The number of the pitches P is equal in the respective loosely wound portions 101. The numbers of windings of the respective loosely wound portions 101 are, for example, equal to each other.

Lengths L of the respective densely wound portions 103 are, for example, equal to each other, amounts of initial tension in the respective densely wound portions 103 are, for example, equal to each other, and the numbers of windings of the respective densely wound portions 103 are, for example, equal and uniform.

Second Modification

Figure 6B:
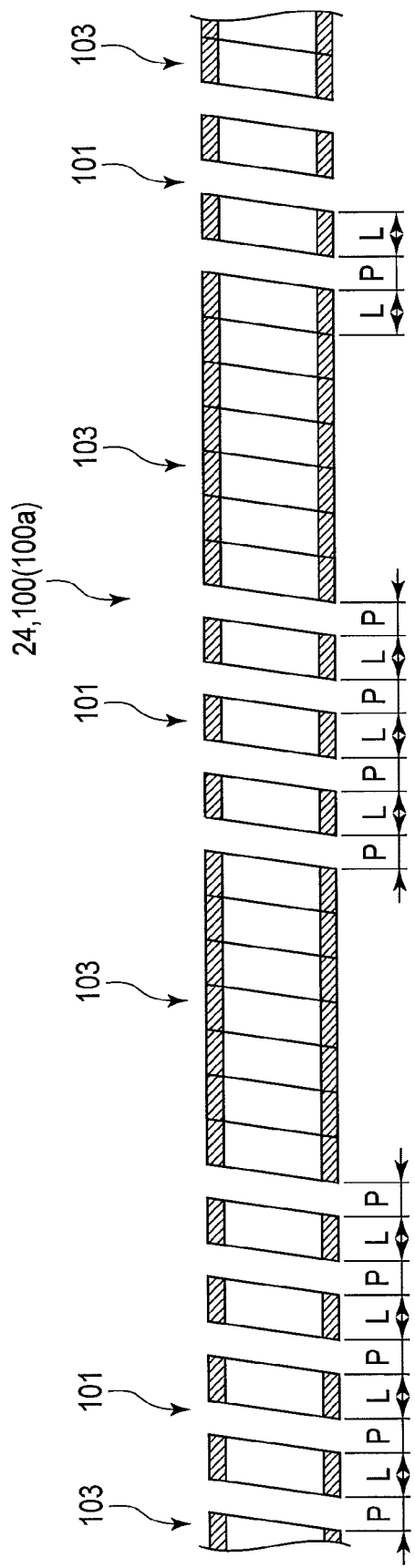
FIG. 6B is a view showing a second modification of the passive bending section.

As shown in FIG. 6B, for example, the number of windings of a loosely wound portion 101 gradually decreases from a distal end portion of a passive bending section 24 toward a proximal end portion of the passive bending section 24.

In this case, lengths L of the respective loosely wound portions 101 are, for example, uniform. Respective pitches P in the loosely wound portion 101 are, for example, equal to each other.

Lengths L of respective densely wound portions 103 are, for example, uniform with each other, amounts of initial tension in the respective densely wound portions 103 are, for example, equal to each other, and the numbers of windings of the respective densely wound portions 103 are, for example, equal to each other.

Third Modification

As shown in FIG. 6C, a length L of a thin plate in a loosely wound portion 101 (a width of a thin plate member 150 forming the loosely wound portion 101) gradually lengthens from a distal end portion of a passive bending section 24 toward a proximal end portion of the passive bending section 24. In detail, each length L1 of the thin plate in the loosely wound portion 101 disposed on an active bending section 23 side is shorter than each length L2 of the thin plate in the loosely wound portion 101 disposed on a flexible tube 25 side.

In this case, respective pitches P are equal to each other. The numbers of the pitches P in each loosely wound portion 101 are the same. The numbers of windings of the respective loosely wound portions 101 are, for example, equal to each other.

Lengths L of respective densely wound portions 103 are, for example, uniform, amounts of initial tension in the respective densely wound portions 103 are, for example, equal to each other, and the numbers of windings of the respective densely wound portions 103 are, for example, equal to each other.

Fourth Modification

As shown in FIG. 6D, initial tension given to a densely wound portion 103 disposed on a distal end portion side is smaller than initial tension given to a densely wound portion 103 disposed on a proximal end portion side. For example, the initial tension given to the densely wound portion 103 gradually increases from the densely wound portion 103 disposed on the distal end portion side toward the densely wound portion 103 disposed on the proximal end portion side.

It is to be noted that the initial tension given to the densely wound portion 103 may gradually increase from a distal end portion of the densely wound portion 103 toward a proximal end portion of the densely wound portion 103 in one densely wound portion 103.

Fifth Modification

Figure 6E:
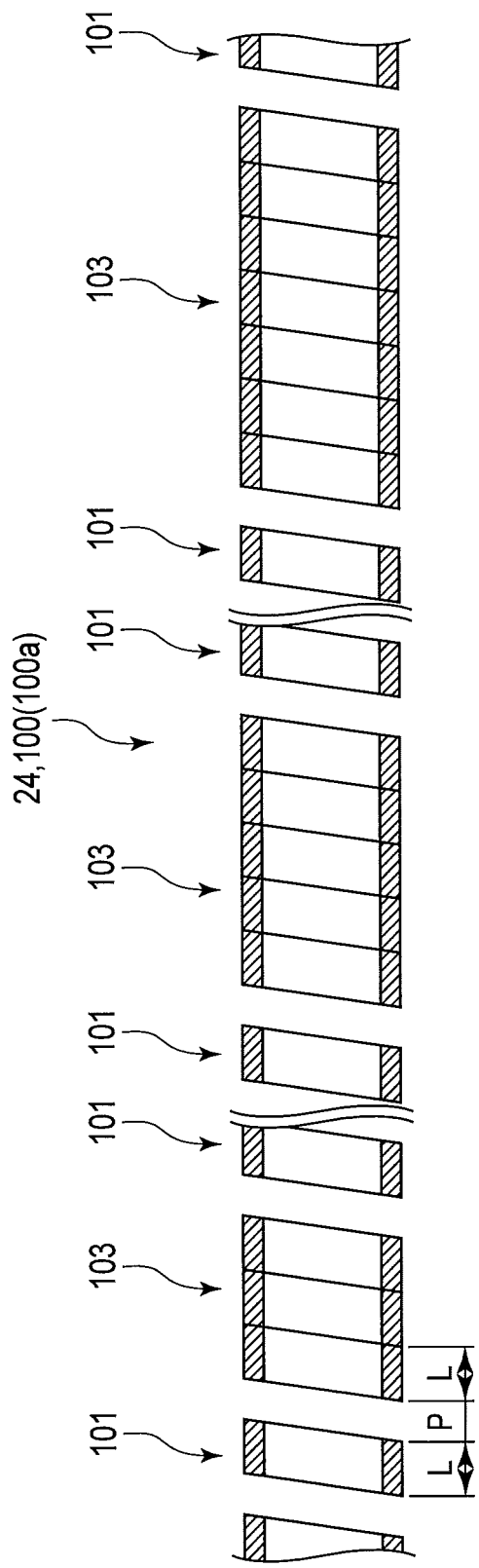
FIG. 6E is a view showing a fifth modification of the passive bending section.

As shown in FIG. 6E, the number of windings of a densely wound portion 103 gradually increases from a distal end portion of a passive bending section 24 toward a proximal end portion of the passive bending section 24. Consequently, a length of the densely wound portion 103 gradually increases from the distal end portion of the passive bending section 24 toward the proximal end portion of the passive bending section 24.

In this cases, pitches P in each loosely wound portion 101 are, for example, equal to each other. Lengths L of the respective loosely wound portions 101 are, for example, uniform. The numbers of windings of the respective loosely wound portions 101 are equal to each other.

Lengths L of the respective densely wound portions 103 are, for example, uniform. For example, amounts of initial tension in the respective densely wound portions 103 are, for example, equal to each other.

Sixth Modification

Figure 6F:
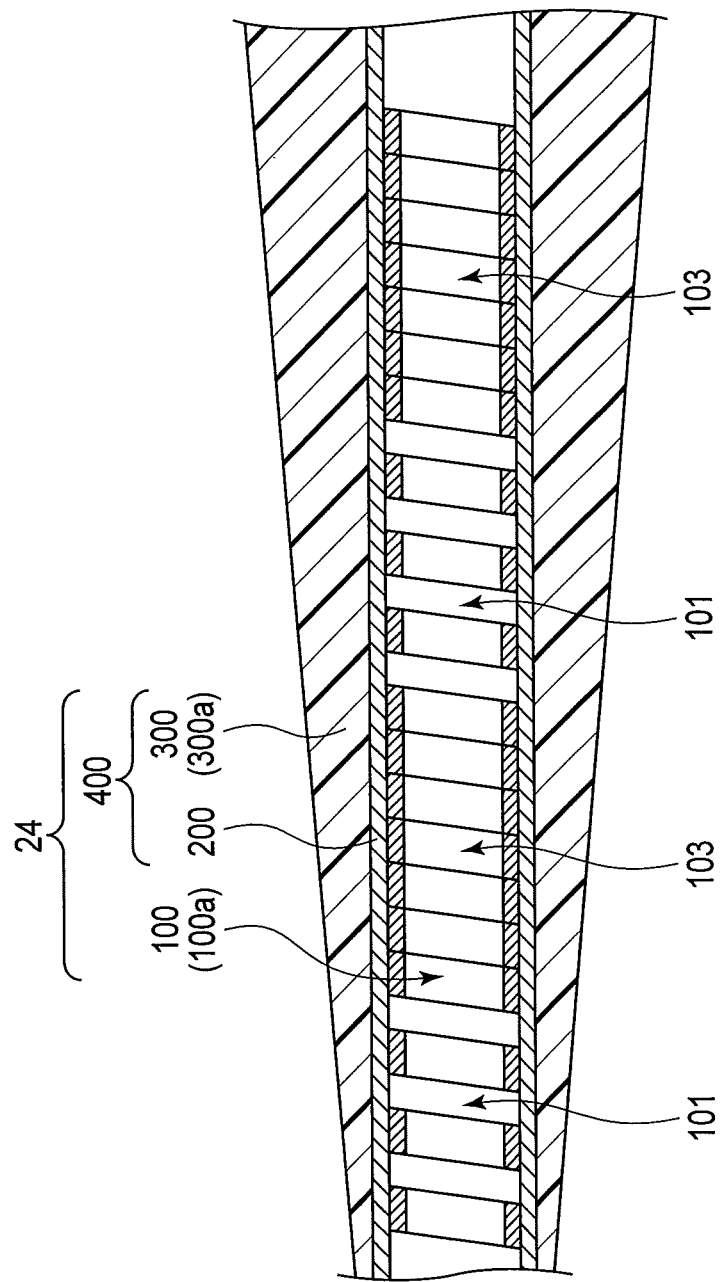
FIG. 6F is a view showing a sixth modification of the passive bending section.

As shown in FIG. 6F, a thickness of an envelope 300a is variable so that a proximal end portion side of the envelope 300a is thicker than a distal end portion side of the envelope 300a. In detail, the thickness of the envelope 300a gradually increases from a distal end portion of the envelope 300a toward a proximal end portion of the envelope 300a.

Seventh Modification

A density of a reticular tube 200 of a passive bending section 24 is variable so that the density of a proximal end portion side of the reticular tube 200 is higher than that of a distal end portion side of the reticular tube 200. In detail, the density of the reticular tube 200 gradually increases from a distal end portion of the reticular tube 200 toward a proximal end portion of the reticular tube 200.

In the above present embodiment and the respective modifications, any mutual combination can be carried out.

The present invention is not limited to the above embodiment as it is, and in the implementation stage, configurational elements can be modified and embodied without departing from the gist thereof. Additionally, various inventions can be formed by any suitable combination of the configurational elements disclosed in the above embodiment.

What is claimed is:

1. An endoscope comprising an operating section, a first helical tube that constitutes a flexible tube connected to the operating section and is disposed along a central axis direction, a first cover that covers an outer peripheral surface of the first helical tube, an active bending section that is disposed on a distal side of the flexible tube and is actively bent by an operation of the operating section, and a passive bending section that is disposed between the flexible tube and the active bending section along the central axis direction and is passively bent by an external force,
   wherein the passive bending section comprises:
   a distal end portion coupled with the active bending section;
   a proximal end portion coupled with the flexible tube;
   a second helical tube continuous with the first helical tube so that loosely wound portions in which thin plates are helically wound via clearances in the central axis direction and densely wound portions in which the thin plates are helically wound by bringing the adjacent thin plates into contact closely with each other in the central axis direction are alternately disposed along the central axis direction; and
   a second cover that covers an outer peripheral surface of the second helical tube, and
   in a first loosely wound portion disposed on a side of the distal end portion of a material forming the second helical tube and a second loosely wound portion disposed on a side of the proximal end portion of the material forming the second helical tube, a flexural rigidity in the second loosely wound portion is larger than a flexural rigidity in the first loosely wound portion,
   a flexural rigidity of the first helical tube is smaller than a flexural rigidity of the second helical tube, and
   the second cover is superimposed on a distal end of the first cover so that an inner peripheral surface of a proximal end of the second cover abuts on an outer peripheral surface of the distal end of the first cover in the flexible tube, and the second cover covers the distal end of the first cover.

2. The endoscope according to claim 1, wherein the second cover is made of a material different from that of the first cover.

3. The endoscope according to claim 1, wherein the first helical tube and the second helical tube are continuously and integrally formed by the helically wound thin plates.

4. The endoscope according to claim 1, wherein the second cover of the passive bending section is extended to the active bending section, and covers the outer peripheral surface of the active bending section.

5. The endoscope according to claim 1, wherein in the material forming the second helical tube, a pitch at which the thin plate is wound in the second loosely wound portion is narrower than a pitch at which the thin plate is wound in the first loosely wound portion, in the first loosely wound portion and the second loosely wound portion.

6. The endoscope according to claim 1, wherein in the densely wound portion of the second helical tube, initial tension is given to the thin plates that come in contact adjacently and closely with each other in the central axis direction.

7. The endoscope according to claim 6, wherein in the second helical tube, the initial tension given to the densely wound portion disposed on the distal end portion side is smaller than the initial tension given to the densely wound portion disposed on the proximal end portion side.

8. The endoscope according to claim 1, wherein the first loosely wound portion is disposed at a distal end of the passive bending section, and the second loosely wound portion is disposed at a proximal end of the passive bending section.

9. The endoscope according to claim 1, wherein the proximal end portion of the passive bending section is coupled to the flexible tube.

10. The endoscope according to claim 1, wherein the distal end portion of the passive bending section is coupled to the active bending section.

11. An endoscope comprising an operating section, a first helical tube that constitutes a flexible tube connected to the operating section and is disposed along a central axis direction, a first cover that covers an outer peripheral surface of the first helical tube, an active bending section that is disposed on a distal side of the flexible tube and is actively bent by an operation of the operating section, and a passive bending section that is disposed between the flexible tube and the active bending section along the central axis direction and is passively bent by an external force,
    wherein the passive bending section comprises:
    a distal end portion coupled with the active bending section;
    a proximal end portion coupled with the flexible tube;
    a second helical tube continuous with the first helical tube so that loosely wound portions in which thin plates are helically wound via clearances in the central axis direction and densely wound portions in which the thin plates are helically wound by bringing the adjacent thin plates into contact closely with each other in the central axis direction are alternately disposed along the central axis direction; and
    a second cover that covers an outer peripheral surface of the second helical tube, and
    in a first loosely wound portion disposed on a side of the distal end portion of a material forming the second helical tube and a second loosely wound portion disposed on a side of the proximal end portion of the material forming the second helical tube, the number of windings of the thin plates wound in the second loosely wound portion is smaller than the number of windings of the thin plates wound in the first loosely wound portion,
    a flexural rigidity of the first helical tube is smaller than a flexural rigidity of the second helical tube, and
    the second cover is superimposed on a distal end of the first cover so that an inner peripheral surface of a proximal end of the second cover abuts on an outer peripheral surface of the distal end of the first cover in the flexible tube, and the second cover covers the distal end of the first cover.

\* \* \* \* \*